United States Patent
Wada et al.

[19]

[11] Patent Number: 6,033,219
[45] Date of Patent: Mar. 7, 2000

[54] RIGID BUR GUARD HAVING A FOAM INSERT FOR PROTECTING INDIVIDUALS FROM INFECTIOUS DENTAL TOOLS

[76] Inventors: Eric Minoru M Wada, 764 W. Lancaster Blvd., Lancaster, Calif. 93534; Bridget K Samp, 40018 Castana La.; Jennifer A Park, 40540 Via Verdad, both of Palmdale, Calif. 93551

[21] Appl. No.: 09/169,659

[22] Filed: Oct. 9, 1998

[51] Int. Cl.[7] ................................................. A61C 1/16
[52] U.S. Cl. ........................ 433/116; 206/63.5; 206/368
[58] Field of Search .................... 433/116, 165, 433/166; 604/192, 263; 600/29, 31, 32; 206/63.5, 368, 369

[56] References Cited

U.S. PATENT DOCUMENTS

| | | | |
|---|---|---|---|
| 2,971,637 | 2/1961 | Simons | 206/369 |
| 3,876,067 | 4/1975 | Schwarz | 206/205 |
| 4,089,537 | 5/1978 | Pralutsky | 280/851 |
| 4,232,784 | 11/1980 | Hesselgren | 206/210 |
| 4,280,808 | 7/1981 | Johnsen | 433/77 |
| 4,286,950 | 9/1981 | Hawk | 433/116 |
| 4,380,292 | 4/1983 | Cramer | 604/192 |
| 4,445,611 | 5/1984 | Shofu | 206/369 |
| 4,446,967 | 5/1984 | Halkyard | 604/263 |
| 4,482,348 | 11/1984 | Dent | 604/263 |
| 4,503,972 | 3/1985 | Nelligan et al. | 206/379 |
| 4,804,090 | 2/1989 | Schuh et al. | 206/366 |
| 5,167,643 | 12/1992 | Lynn | 604/263 |
| 5,267,861 | 12/1993 | Daemer | 433/116 |
| 5,338,195 | 8/1994 | Flannagen | 433/116 |
| 5,358,112 | 10/1994 | Gardner | 206/369 |
| 5,376,003 | 12/1994 | Rizkalla | 433/116 |
| 5,554,127 | 9/1996 | Crouther et al. | 604/192 |
| 5,769,223 | 6/1998 | Marsh | 206/365 |
| 5,797,885 | 8/1998 | Rubin | 604/192 |

*Primary Examiner*—Nicholas D. Lucchesi
*Attorney, Agent, or Firm*—Dennis Beech

[57] ABSTRACT

The bur guard covers and removes foreign matter from burs protruding from a dental hand piece with an outer member, a foam inner member, and a mechanism to hold the foam taut enough to accept any bur shape, size, or texture thus, increasing the effectiveness of the bur and the efficiency of the dental procedure and while in position over the bur, will protect the dentist, dental assistant, and patient from a potentially infectious laceration or puncture wound.

6 Claims, 2 Drawing Sheets

6,033,219

RIGID BUR GUARD HAVING A FOAM INSERT FOR PROTECTING INDIVIDUALS FROM INFECTIOUS DENTAL TOOLS

BACKGROUND OF THE INVENTION

1. Field of the Invention

This invention relates to dental equipment and is especially directed toward devices that protect the dentist, assistant, and patient from potentially infectious, even fatal punctures and lacerations from dental burs utilized during dental procedures.

2. Description of Related Art

It is common practice for dentists to use dental instruments or tools having a hand piece, slow and high speed, for the removal of tooth decay. The burs inserted into these hand pieces come in a variety of shapes and sizes; however, one thing they all share is the accumulation of infectious matter during cavity removal. The blood, saliva, and tooth debris that form the aggregate of infectious matter can be teeming with bacterial and viral activity.

With communicable diseases such as AIDS, tuberculosis, and hepatitis still prevalent in society, it becomes obvious that the need for prevention of contamination and injury from dental burs is necessary. It is an all to frequent occurrence for the dentist, dental assistant, and even the patient to rake their hand, arm, or other part of their body across an unprotected bur in the dental hand piece. This can be as lethal as an infectious needle prick or puncture. OSHA requires that all needles be covered while not in use. The dental bur should also be covered while not in use and in the hand piece.

Currently, there are dental devices that clean the dental burs after the dental procedure is completed. Also, there is a device in the field of endodontics that remove foreign matter from endodontic files, allows measurement of length, and stores them while not in use. This is accomplished by inserting a triangle piece of foam into a plastic holder. However, none of the previous devices provide a mechanism that will hold the foam inserts taut enough to accept various shape, size or texture of burs.

The instant invention is designed specifically to prevent dental burs, while in a hand piece, from lacerating, puncturing, and possibly infecting the dentist, the dental assistant or others. In addition, the bur guard protects the patient from inadvertently scratching, puncturing, or cutting themselves. Finally, the bur guard removes infectious debris from the burs and thereby increase the effectiveness of the bur while cutting and drilling. Numerous devices have been proposed for accomplishing this purpose; however, many of the previous devices have been complex, ineffective, and difficult to use.

The bur guard is designed specifically to accept a variety of bur shape, size, or texture devices. Also, the present invention is disposable and is intended to be used throughout the dental procedure thus making the bur more effective and the procedure more efficient. In addition, the bur guard will prevent the dentist, dental assistant, and patient from inadvertently scraping, puncturing, or lacerating themselves.

SUMMARY OF THE INVENTION

The primary object of the present invention is to provide protection for the dentist, assistant, and patient from an unguarded and exposed dental bur protruding from a dental handpiece. Another object of the present invention is to prevent contamination and cross contamination by removing foreign matter from an unguarded bur. A further object of the present invention is to eliminate excess debris from the bur, thereby increasing the burs cutting effectiveness. Another object of the present invention is to increase the efficiency of the dental procedure. Another object of the present invention is that it is simple in construction. Another object of the present invention is that it is compact in size. Another object of the present invention is that it is easy to install. Another object of the present invention is that it is disposable. Another object of the present invention is that it is inexpensive. A final object of the present. invention is that it is simple to manufacture.

In accordance with the description presented herein, other objectives of this invention will become apparent when the description and drawings are reviewed.

DESCRIPTION OF THE PREFERRED EMBODIMENT

The bur guard is an apparatus for covering burs used with dental instruments or tools and which burs are normally attached to the operating end of a dental hand piece of such tools. The process of inserting and removing a bur from the bur guard acts to remove foreign matter from the bur. The bur guard consists of an outer member or case containing a foam insert member therein and having a mechanism for retaining the foam insert taut to allow penetration by a bur and retention on the bur. In the description of the preferred embodiment the foam retaining mechanism is illustrated as a movable cover or lid. While the bur guard is in position over the burs it protects the dentist, dental assistant, patient and others from a potentially infectious or serious laceration wound.

Figure 1:
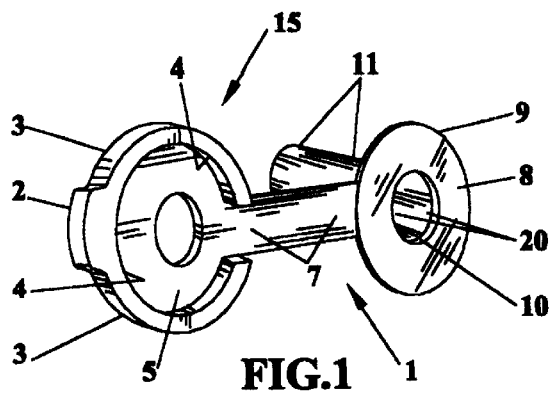
FIG. 1 is a perspective view of the present invention and illustrates an outer member that is attached at its rim to a cap.

Reference is made first to FIG. 1 of the drawings which illustrates a bur guard 1 with an outer member 11 of cylindrical shape comprised of a central section 10 that is hollow with a base end 21 and an open proximal end 20 and having at its proximal end 20 a rim 8 radially attached thereto. The rim 8 is convex at its peripheral edge 9 and is attached by a band or hinge 7 to a cap 15. The cap 15 is comprised of an internal flat surface 5 and has an outer rim 3 that is concave on its interior face 4. This allows the outer rim 3 of the cap 15 to be snapped over the peripheral edge 9 of the rim 8. The cap 15 can be easily removed from the rim 8 by pulling on the tab 2. The cap 15 has an aperture 6 at its center.

Figure 2:
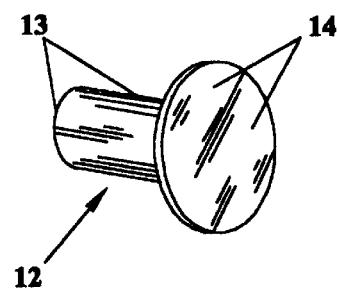
FIG. 2 is a perspective view of the disposable foam inner member.
Figure 3:
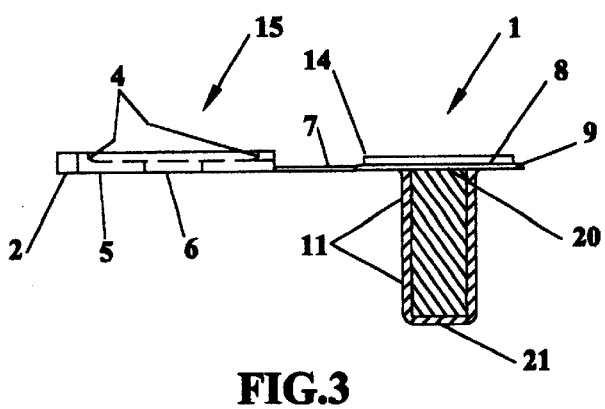
FIG. 3 is a cross sectional view of the present invention.

FIG. 2 illustrates the foam insert member 12 comprised of a tubular portion 13 and a flat end portion 14. FIG. 3 is a cross sectional view of the bur guard 1 with the cap 15 in the open position with the flat end portion 14 of the foam insert member 12 resting atop the rim 8 of the outer member 11.

Figure 4:
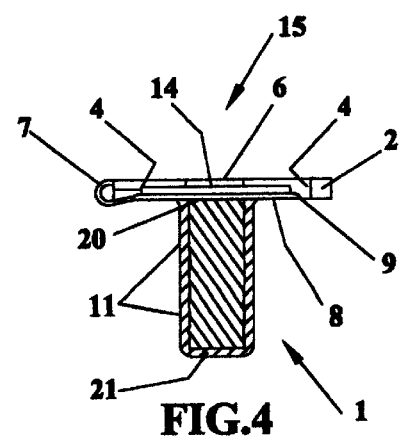
FIG. 4 is a cross-sectional view of the present invention with the disposable foam inner member in place, retained and held taut by the attached cap.

FIG. 4 illustrates the bur guard 1 with the cap 15 snapped over the rim 8 of the outer member 11. In this position the tubular portion 13 of the foam insert member 12 occupies the central section 10 of the outer member 11. Also, the flat end portion 14 of the foam insert member 12 is sandwiched tightly between the rim 8 of the outer member 11 and the flat surface 5 of the cap 15. The cap 15 has aperture 6 thereby exposing only a very taut portion of the foam insert member 12. This structure allows bur shape, size or texture variations to penetrate its surface and upon insertion and withdrawal of the dental burs from the foam insert member 12 to remove excess debris or foreign matter. Also, while the bur guard 1 is in position over the bur, the dentist, assistant, and patient are protected from an infectious laceration or puncture wound. The foam insert member is formed of a foam-like or foam material such as rubber, synthetic rubber, plastic, various polymers as, polyurethane, polypropylene or like material of a non-rigid composition which is resilient such that the material bulges against any inserted bur device yet allows penetration for insertion of the bur device.

Figure 5:
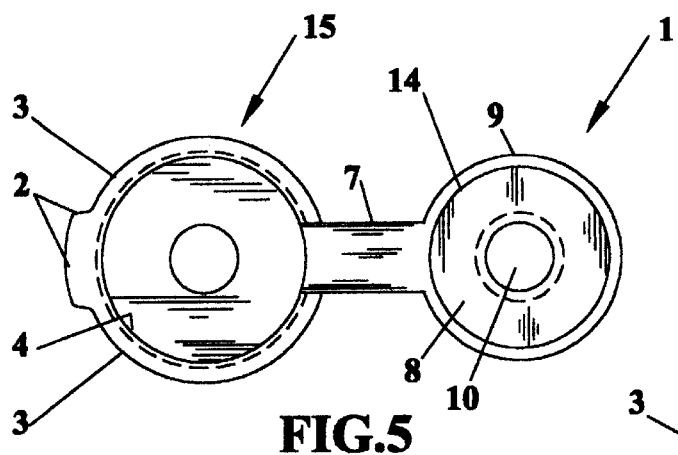
FIG. 5 is an end view of the present invention illustrating the cap opened with the outer member being hollow at its center.
Figure 6:
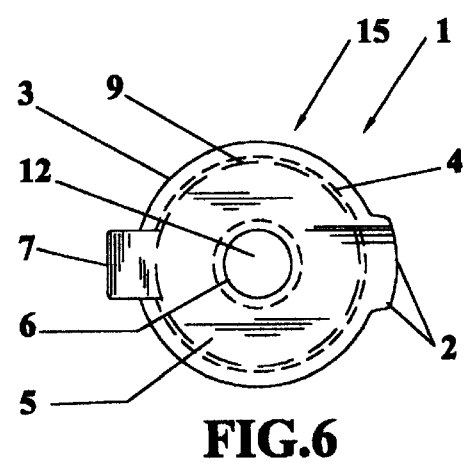
FIG. 6 is an end view of the present invention illustrating the cap closed with the foam inner member sandwiched and held taut by the cap.

FIGS. 5 and 6 are end views of FIGS. 3 and 4 respectively. In these views the tab 2 on the cap 15 is clearly visible. The tab 2 end of the cap 15 is easily removable from the rim 8 and its outer member 11.

Figure 7:
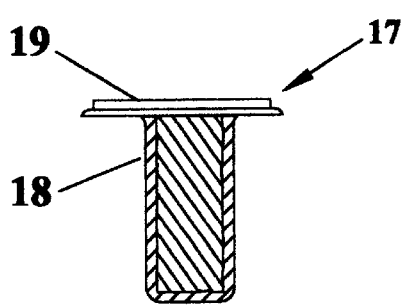
FIG. 7 is a cross sectional view of the present invention as a one-piece disposable apparatus

FIG. 7 illustrates the bur guard 17, as a one-piece disposable apparatus comprised of a central section 18 and a rim 19 at the proximal end.

Figure 8:
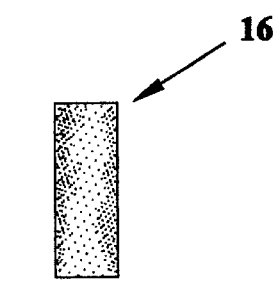
FIG. 8 is a side view of the injectable foam insert material.

FIG. 8 illustrates a view of the injectable foam material 16.

Figure 9:
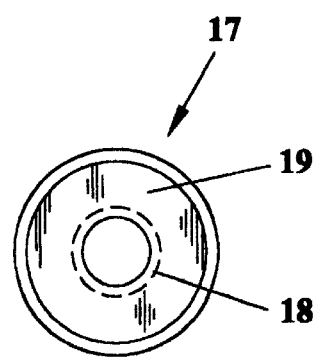
FIG. 9 is a end view of the present invention as a one piece apparatus with the injectable foam insert material in place and contiguous with the inner surface of the center section.

FIG. 9 illustrates an end view with the foam material in place and contiguous with the internal surface of the central section 18.

What is claimed is:

1. An apparatus for covering dental burs and for removing foreign matter therefrom comprising:

an outer member having a hollow interior with a base end and an open end with a foam insert member of solid material contained therein; and the foam insert member having a flat end portion which is retained by a means for attachment to maintain the flat end portion taut when pressure is applied to the flat end portion.

2. The apparatus as in claim 1 wherein the foam insert member removably inserted in the outer member and the means for attachment comprising:

a rim formed radially around the open end and having attached by a hinge a cap;

the cap having an outer rim with a concave interior face for mating with a peripheral edge of the rim such that when the cap is closed over the rim the flat end portion is sandwiched between and retained by the pressure between the cap and the rim; and the cap having an aperture defined therein.

3. The apparatus as in claim 2 wherein the foam insert member is formed of a non-rigid composition material which is resilient such that the material allows penetration and bulges against insertable dental burs.

4. The apparatus as in claim 2 wherein there is a tab on the outer rim.

5. An apparatus for covering dental burs and for removing foreign matter therefrom comprising;

an outer member having a hollow interior with a base end and an open end with a foam insert member of solid material contained therein wherein the foam insert member is fixedly attached to the interior walls of the outer member to maintain the foam insert member taut.

6. The apparatus as in claim 5 wherein the foam insert member is formed of a non-rigid composition material which is resilient such that the material allows penetration and bulges against insertable dental burs.

* * * * *